(12) United States Patent
Kong et al.

(10) Patent No.: US 12,078,631 B2
(45) Date of Patent: Sep. 3, 2024

(54) SAMPLE ANALYSIS APPARATUS AND SAMPLE ANALYSIS METHOD (71) Applicant: Shenzhen Mindray Animal Medical Technology Co., Ltd., Guangdong (CN)

(72) Inventors: Fangang Kong, Shenzhen (CN); Xinjun Zhang, Shenzhen (CN); Weiwei Yan, Shenzhen (CN); Shaojian Liu, Shenzhen (CN)

(73) Assignee: Shenzhen Mindray Animal Medical Technology Co., Ltd., Shenzhen (CN)

( * ) Notice: Subject to any disclaimer, the term of this patent is extended or adjusted under 35 U.S.C. 154(b) by 52 days.

(21) Appl. No.: 18/091,220

(22) Filed: Dec. 29, 2022

(65) Prior Publication Data
US 2023/0143409 A1 May 11, 2023

Related U.S. Application Data (63) Continuation of application No. PCT/CN2021/115674, filed on Aug. 31, 2021.

(51) Int. Cl.
*G01N 33/50* (2006.01)
*G01N 35/00* (2006.01)
*G01N 35/10* (2006.01)
*G01N 15/01* (2024.01)

(52) U.S. Cl.
CPC ... *G01N 33/5005* (2013.01); *G01N 35/00584* (2013.01); *G01N 35/1002* (2013.01); *G01N 2015/016* (2024.01); *G01N 2035/00851* (2013.01); *G01N 2035/00891* (2013.01)

(58) Field of Classification Search
CPC ......... G01N 33/5005; G01N 35/00584; G01N 35/1002; G01N 2015/008; G01N 2035/00851; G01N 2035/00891
See application file for complete search history.

(56) References Cited

U.S. PATENT DOCUMENTS

| 5,125,737 A | * | 6/1992 | Rodriguez | G01N 15/1459 356/338 |
| 5,882,933 A | * | 3/1999 | Li | G01N 15/1459 436/63 |
| 6,391,263 B1 | | 5/2002 | Mishima | |

(Continued)

FOREIGN PATENT DOCUMENTS

| CN | 1030481 A | 1/1989 |
| CN | 1774631 A | 5/2006 |

(Continued)

*Primary Examiner* — P. Kathryn Wright
(74) *Attorney, Agent, or Firm* — Leydig, Voit & Mayer, Ltd.

(57) ABSTRACT

Disclosed are a sample analysis apparatus and a sample analysis method. The method includes: obtaining a leukocyte measurement mode for a test sample, the method having a plurality of leukocyte measurement modes, each of which includes at least a reaction time, and different leukocyte measurement modes having different reaction times; determining a reaction time for the current sample to be tested; controlling the sample to be tested to react with the reagent, to prepare a test sample for detecting leukocytes; and controlling to detect the test sample for detecting leukocytes, to obtain detection data of leukocyte classification.

7 Claims, 8 Drawing Sheets (56) References Cited

U.S. PATENT DOCUMENTS

| | | | |
|---|---|---|---|
| 2011/0027826 A1* | 2/2011 | Fukuya | G01N 33/5094 435/39 |
| 2015/0125900 A1* | 5/2015 | Nagai | G01N 33/5091 436/66 |
| 2018/0188236 A1 | 7/2018 | Nagai et al. | |
| 2021/0041341 A1* | 2/2021 | Chen | G01N 15/1459 |

FOREIGN PATENT DOCUMENTS

| | | | |
|---|---|---|---|
| CN | 101097180 A | | 1/2008 |
| CN | 101236195 A | | 8/2008 |
| CN | 101535804 A | | 9/2009 |
| CN | 103837502 A | | 6/2014 |
| CN | 105310657 A | | 2/2016 |
| CN | 107686859 A | | 2/2018 |
| CN | 111656188 A | | 9/2020 |
| CN | 111912770 A | | 11/2020 |
| CN | 111912978 A | * | 11/2020 |
| CN | 112114000 A | | 12/2020 |
| WO | 2011038509 A1 | | 4/2011 |
| WO | WO-2019206298 A1 * | 10/2019 | G01N 15/1459 |
| WO | 2020252701 A1 | | 12/2020 |
| WO | 2021051349 A1 | | 3/2021 |

* cited by examiner

SAMPLE ANALYSIS APPARATUS AND SAMPLE ANALYSIS METHOD

CROSS-REFERENCE TO RELATED APPLICATIONS

This application is a continuation of International Application No. PCT/CN2021/115674, filed on Aug. 31, 2021, which is incorporated herein by reference in its entirety.

TECHNICAL FIELD

The disclosure relates to the field of in vitro diagnostics, and in particular to a sample analysis apparatus and a sample analysis method.

BACKGROUND

A sample analysis apparatus, for example, a sample analysis apparatus for a body fluid or blood, can be used to test cell particles in the blood and the body fluid, for example, can be used to count and classify white blood cells (WBCs), red blood cells (RBCs), platelets (PLTs), nucleated red blood cells (NRBCs), reticulocytes (RETs), and other cell particles.

White blood cells include neutrophils, lymphocytes, monocytes, eosinophils and eosinophils. It is of great significance to classify and count white blood cells in clinical diagnosis. A test procedure is as follows: a sample (a body fluid or blood sample) is treated with a hemolytic agent to hemolyze red blood cells therein into ghosts (or in other words, erythrocyte fragments), so as to prevent interference with classification and counting of white blood cells.

During classification and counting of white blood cells, results of some samples are abnormal.

SUMMARY

In order to solve the above problems, the disclosure mainly provides a sample analysis apparatus and a sample analysis method, which will be described in detail below.

According to a first aspect, an embodiment provides a sample analysis apparatus. The sample analysis apparatus is configured to analyze samples of one or more animals and has a plurality of leukocyte measurement modes for at least one of the animals, where each of the leukocyte measurement modes includes at least a reaction time, and different leukocyte measurement modes for a same animal have different reaction times; the sample analysis apparatus includes:
  a sample supply portion configured to supply a sample;
  a reagent supply portion configured to supply a reagent;
  a reaction portion configured to provide a reaction place for the sample and the reagent so as to prepare a test sample formed by reaction of the sample and the reagent;
  a detection portion configured to detect the test sample so as to obtain detection data; and
  a processor configured to calculate a detection result according to the detection data;
  wherein
  the processor obtains a current leukocyte measurement mode for a sample to be tested;
  the processor sets a reaction time for the sample to be tested according to the current leukocyte measurement mode for the sample to be tested;
  the processor controls the sample supply portion to provide the sample to be tested to the reaction portion, and controls the reagent supply portion to provide a reagent containing a hemolytic agent to the reaction portion;
  the processor controls, according to the set reaction time for the sample to be tested, the sample to be tested and the reagent to react in the reaction portion so as to prepare a test sample for detecting leukocytes; and
  the processor controls the detection portion to detect the test sample so as to obtain detection data of leukocyte classification.

In an embodiment, each of the leukocyte measurement modes further includes a leukocyte classification algorithm, and different leukocyte measurement modes for a same animal have different leukocyte classification algorithms; and
  the processor processes the detection data of leukocyte classification according to the leukocyte classification algorithm for the current leukocyte measurement mode for the sample to be tested, so as to obtain a detection result of leukocyte classification.

In an embodiment, the processor determines whether ghosts interfere with the detection result of leukocyte classification according to the detection data of leukocyte classification; and if yes, the processor controls to send out a prompt that the ghosts interfere with the result of leukocyte classification, and/or controls to send out a prompt for a user to switch the leukocyte measurement mode.

In an embodiment, when determining that the ghosts interfere with the detection result of leukocyte classification, the processor further controls to retest the sample to be tested in a mode different from the current leukocyte measurement mode for the sample to be tested.

In an embodiment, the reaction time of the leukocyte measurement mode during the retest of the sample to be tested is greater than that of the leukocyte measurement mode before the sample to be tested is retested.

In an embodiment, the processor is further capable of generating a leukocyte measurement mode setting interface configured to be operable by a user to set a leukocyte measurement mode for an animal.

In an embodiment, the leukocyte measurement mode setting interface includes an animal type entry operable by a user to set an animal type, and a reaction time entry operable by the user to set a leukocyte measurement mode corresponding to the animal type.

In an embodiment, the processor is further capable of generating a sample requesting interface operable by a user to set a sample to be tested to be of a corresponding animal type.

According to a second aspect, an embodiment provides a sample analysis apparatus having a plurality of leukocyte measurement modes. Each of the leukocyte measurement modes includes at least a reaction time, and different leukocyte measurement modes have different reaction times; the sample analysis apparatus includes:
  a sample supply portion configured to supply a sample;
  a reagent supply portion configured to supply a reagent;
  a reaction portion configured to provide a reaction place for the sample and the reagent so as to prepare a test sample formed by reaction of the sample and the reagent;
  a detection portion configured to detect the test sample so as to obtain detection data; and
  a processor configured to calculate a detection result according to the detection data;
  wherein the processor obtains a current leukocyte measurement mode for a sample to be tested;

the processor sets a reaction time for the sample to be tested according to the current leukocyte measurement mode for the sample to be tested;

the processor controls the sample supply portion to provide the sample to be tested to the reaction portion, and controls the reagent supply portion to provide a reagent containing a hemolytic agent to the reaction portion;

the processor controls, according to the set reaction time for the sample to be tested, the sample to be tested and the reagent to react in the reaction portion so as to prepare a test sample for detecting leukocytes; and the processor controls the detection portion to detect the test sample so as to obtain detection data of leukocyte classification.

In an embodiment, each of the leukocyte measurement modes further includes a leukocyte classification algorithm, and different leukocyte measurement modes have different leukocyte classification algorithms; and the processor processes the detection data of leukocyte classification according to the leukocyte classification algorithm of the current leukocyte measurement mode for the sample to be tested, so as to obtain a detection result of leukocyte classification.

In an embodiment, the processor determines whether ghosts interfere with the detection result of leukocyte classification according to the detection data of leukocyte classification; and if yes, the processor controls to send out a prompt that the ghosts interfere with the result of leukocyte classification, and/or controls to send out a prompt for a user to switch the leukocyte measurement mode.

In an embodiment, when the processor determines that the ghosts interfere with the detection result of leukocyte classification, the processor further controls to retest the sample to be tested in a mode different from the current leukocyte measurement mode for the sample to be tested.

In an embodiment, the reaction time of the leukocyte measurement mode during the retest of the sample to be tested is greater than that of the leukocyte measurement mode before the sample to be tested is retested.

In an embodiment, the processor is further capable of generating a leukocyte measurement mode setting interface for samples configured to be operable by a user to set a sample to be tested to be of a corresponding leukocyte measurement mode.

According to a third aspect, an embodiment provides a sample analysis method, including:

obtaining a leukocyte measurement mode for a current sample to be tested, wherein the sample analysis method has a plurality of leukocyte measurement modes, each of the leukocyte measurement modes includes at least a reaction time, and different leukocyte measurement modes have different reaction times;

determining, according to the leukocyte measurement mode for the current sample to be tested, a reaction time for the current sample to be tested;

controlling, according to the determined reaction time for the sample to be tested, the sample to be tested to react with a reagent containing a hemolytic agent, so as to prepare a test sample for detecting leukocytes; and controlling to detect the test sample for detecting leukocytes, so as to obtain detection data of leukocyte classification.

In an embodiment, each of the leukocyte measurement modes further includes a leukocyte classification algorithm, and different leukocyte measurement modes have different leukocyte classification algorithms; and the sample analysis method further includes:

processing the detection data of leukocyte classification according to the leukocyte classification algorithm of the current leukocyte measurement mode for the sample to be tested, so as to obtain a detection result of leukocyte classification.

In an embodiment, the sample analysis method further includes:

determining whether ghosts interfere with the detection result of leukocyte classification according to the detection data of leukocyte classification;

if yes, controlling to send out a prompt that the ghosts interfere with the result of leukocyte classification, and/or controlling to send out a prompt for a user to switch the leukocyte measurement mode.

In an embodiment, when it is determined that the ghosts interfere with the detection result of leukocyte classification, the sample to be tested is further controlled to be retested in a mode different from the current leukocyte measurement mode for the sample to be tested.

In an embodiment, the reaction time of the leukocyte measurement mode during the retest of the sample to be tested is greater than that of the leukocyte measurement mode before the sample to be tested is retested.

In an embodiment, the sample analysis method further includes:

generating and displaying, in response to a retest instruction, a leukocyte measurement mode setting interface; the leukocyte measurement mode setting interface displaying the reaction time before the sample to be tested is retested; and setting, in response to an operation on the leukocyte measurement mode setting interface, the leukocyte measurement mode during the retest of the sample to be tested.

According to a fourth aspect, an embodiment provides a computer-readable storage medium storing a program, the program being executable by a processor to implement the method described in any one of the embodiments herein.

DESCRIPTION OF THE PREFERRED EMBODIMENTS

The disclosure will be further described in detail below through specific implementations in conjunction with the accompanying drawings. Associated similar element reference numerals are used for similar elements in different implementations. In the following implementations, many details are described such that the disclosure may be better understood. However, it may be readily appreciated by persons skilled in the art that some of the features may be omitted, or may be substituted by other elements, materials, and methods in different cases. In certain cases, some operations involved in the disclosure are not displayed or described in the specification, which is to prevent a core part of the disclosure from being obscured by excessive description. Moreover, for persons skilled in the art, the detailed description of these involved operations is not necessary, and the involved operations can be thoroughly understood according to the description in the specification and general technical knowledge in the art.

In addition, the characteristics, operations, or features described in the specification may be combined in any appropriate manner to form various implementations. Meanwhile, the steps or actions in the method description may also be exchanged or adjusted in their order in a way that is known to persons skilled in the art. Therefore, the various orders in the specification and the accompanying drawings are merely for the purpose of clear description of a certain embodiment, and are not meant to be a necessary order unless it is otherwise stated that a certain order must be followed.

The serial numbers themselves for the components herein, for example, "first" and "second", etc., are merely used to distinguish the described objects, and do not have any sequential or technical meaning. Moreover, as used in the disclosure, "connection" or "coupling", unless otherwise stated, includes both direct and indirect connections (couplings).

The samples in the disclosure include blood samples and body fluids. The applicant found the situation that during the test of samples, the classification of white blood cells for some samples was seriously interfered with ghosts. It was found through further study that this situation will likewise appear for different subspecies of a same animal, and furthermore, it was found that this situation was also affected by animal raising conditions, etc. It should be noted that animals in the disclosure also include human.

If such problems are solved only by subsequent re-detection, not only will samples and reagents be wasted, but also the time of waiting for sample results will be longer. Also, for an instrument that does not have automatic re-detection and retest functions, it is required to waste manpower to manually take back samples and place them into an instrument again for re-detection and retest.

In view of these above problems, the disclosure provides a sample analysis apparatus that has at least two or more leukocyte measurement modes, these leukocyte measurement modes being different at least in reaction time for a sample and a reagent. By prolonging the reaction time, fragments or in other words, ghosts formed by red blood cells under the action of a hemolytic agent can be small enough not to affect classification and counting of white blood cells. In addition, considering measurement speed and efficiency, various leukocyte measurement modes are set to balance the efficiency and accuracy of results. Detailed description is given below.

Figure 1:
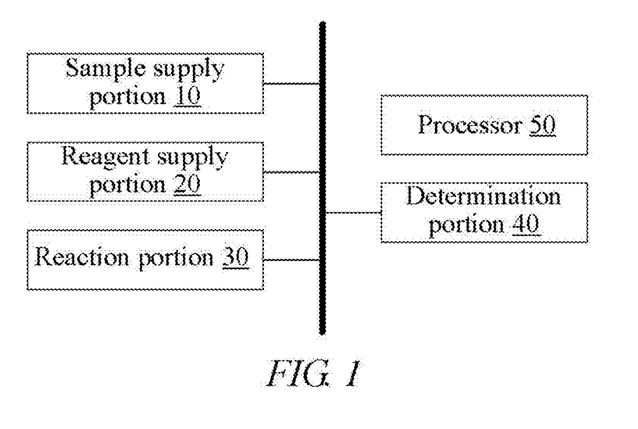
FIG. 1 is a structural schematic diagram of a sample analysis apparatus according to an embodiment.

A sample analysis apparatus is disclosed in some embodiments of the disclosure. Referring to FIG. 1, a sample analysis apparatus in some embodiments includes a sample supply portion 10, a reagent supply portion 20, a reaction portion 30, a detection portion 40, and a processor 50. In some specific embodiments, the sample supply portion 10 is configured to supply a sample; the sample may be a blood sample or a body fluid sample; the body fluid sample may be, for example, a cerebrospinal fluid, a pleural fluid, an ascites fluid, a pericardial sac fluid, a joint fluid, a dialysate for peritoneal dialysis or an intraperitoneal cleaning fluid, etc.; the reagent supply portion 20 is configured to supply a reagent, such as a hemolytic agent, a fluorescent agent and/or a diluent, etc.; the reaction portion 30 is configured to provide a reaction place for the sample and the reagent so as to prepare a test sample formed by reaction of the sample and the reagent; the detection portion 40 is configured to detect the prepared test sample, or in other words, to detect the test sample so as to obtain detection data; and the processor 50 is configured to calculate a detection result according to the detection data. The processor 50 in some embodiments of the disclosure includes, but is not limited to, a central processing unit (CPU), a micro controller unit (MCU), a field-programmable gate array (FPGA), a digital signal processor (DSP) and other apparatuses for interpreting computer instructions and processing data in computer software. In some embodiments, the processor 50 is configured to execute each computer application program in a non-transitory computer-readable storage medium, such that the sample analysis apparatus executes a corresponding test procedure.

Each component is further described below.

In some embodiments, the sample supply portion 10 may include a sample needle which performs a two-dimensional or three-dimensional movement in space by means of a two-dimensional or three-dimensional driving mechanism, such that the sample needle may move to aspirate a sample in a container (such as a sample tube) carrying the sample, then move to, for example, the reaction portion 30, which is configured to provide a reaction place for the sample to be tested and the reagent, and add the sample to the reaction portion 30.

In some embodiments, the reagent supply portion 20 may include a region for carrying a reagent container and a reagent liquid path communicating the reagent container with the reaction portion 30, where a reagent is added from the reagent container to the reaction portion 30 through the reagent liquid path. In some embodiments, the reagent supply portion 20 may also include a reagent needle which performs a two-dimensional or three-dimensional movement in space by means of a two-dimensional or three-dimensional driving mechanism, such that the reagent needle may move to aspirate a reagent in a reagent container, then move to, for example, the reaction portion 30, which is configured to provide a reaction place for the sample to be tested and the reagent, and add the reagent to the reaction portion 30.

The reaction portion 30 may include one or more reaction cells. The reaction portion 30 is configured to provide a treatment place or in other words, a reaction place for the sample and the reagent. A same reaction cell may be shared for different test items. Different reaction cells may also be used for different test items.

A test sample to be tested may be obtained by treating the sample with the reagent. In some embodiments, the reagent includes one or more of a hemolytic agent, a fluorescent agent, and a diluent. The hemolytic agent is a reagent capable of hemolyzing red blood cells in a blood sample and a body fluid sample. Specifically, the hemolytic agent may be any one or a combination of a cationic surfactant, a non-ionic surfactant, an anionic surfactant and an amphiphilic surfactant. The fluorescent agent is used to stain blood cells, and the specific type is selected depending on the test items. An isotonic electrolyte diluent may be used to maintain the morphology of cell particles, so as to prepare a test sample for counting with an impedance method, etc.

Figure 2:
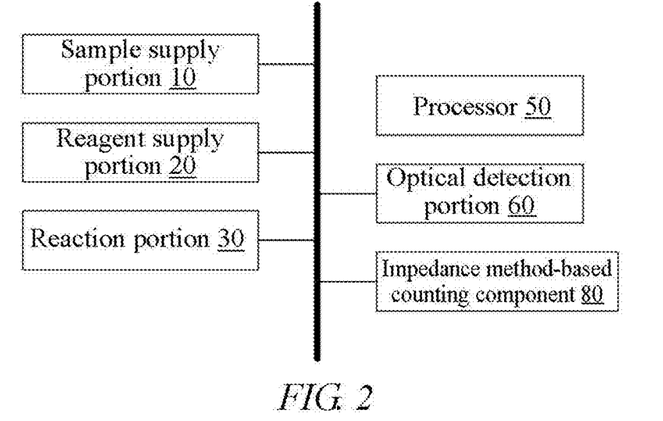
FIG. 2 is a structural schematic diagram of a sample analysis apparatus according to an embodiment.

In some embodiments, referring to FIG. 2, the detection portion 40 includes an optical detection portion 60 and/or an impedance method-based counting component 80, which will be specifically described below.

In some embodiments, the detection portion 40 may include the optical detection portion 60, and the optical detection portion 60 is capable of detecting a sample by using laser scattering principle, and the principle thereof is as follows: irradiating cells by laser light, and performing classification and counting, etc. of the cells by collecting optical signals generated after the cells are irradiated, such as scattered light and fluorescence. Of course, in some embodiments, if the cells are not treated with the fluorescent agent, no fluorescence can be particularly collected. The optical detection portion 60 in the detection portion 40 will be described below.

In some embodiments, the optical detection portion 60 is capable of detecting a sample by using the laser scattering principle, and the principle thereof is as follows: irradiating cells by laser light, and performing classification and counting, etc., of the cells by collecting optical signals generated after the cells are irradiated, such as scattered light and/or fluorescence. Of course, in some embodiments, if the cells are not treated with the fluorescent agent, no fluorescence can be particularly collected. The optical detection portion 60 in the detection portion 40 will be described below.

Figure 3:
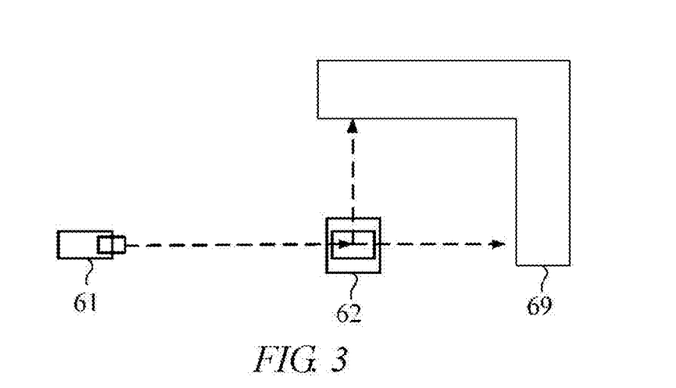
FIG. 3 is a structural schematic diagram of an optical detection portion according to an embodiment.
Figure 4:
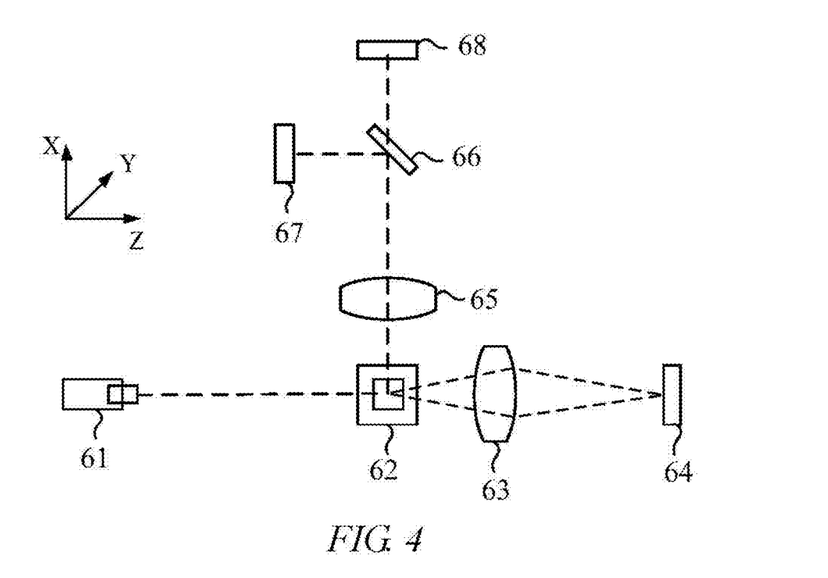
FIG. 4 is a structural schematic diagram of an optical detection portion according to an embodiment.

Referring to FIG. 3, the optical detection portion 60 may include a light source 61, a flow cell 62, and an optical detector 69. The flow cell 62 is in communication with the reaction portion 30 and is configured to allow cells in the test sample to be tested to pass through one by one; and the light source 61 is configured to irradiate the cells passing through the flow cell 62, and the optical detector 69 is configured to obtain optical signals of the cells passing through the flow cell 62. FIG. 4 shows a specific example of the optical detection portion 60. The optical detector 69 may include a lens group 63 for collecting forward-scattered light, a photoelectric detector 64 for converting the collected forward-scattered light from an optical signal to an electrical signal, a lens group 65 for collecting side-scattered light and side fluorescence, a dichroscope 66, a photoelectric detector 67 for converting the collected side-scattered light from an optical signal to an electrical signal, and a photoelectric detector 68 for converting the collected side fluorescence from an optical signal to an electrical signal; and the dichroscope 66 is configured to split light, which is to divide the mixed side-scattered light and side fluorescence into two paths, one path is the side-scattered light, and the other path is the side fluorescence. It should be noted that the optical signals herein may be either optical signals or electrical signals converted from the optical signals, and the optical signals and electrical signals are essentially the same in information contained in representing cell detection results.

The structure of the optical detection portion 60 shown in FIG. 4 is used as an example to explain how the optical detection portion 60 specifically obtains optical signals of the test sample to be tested.

Figure 5:
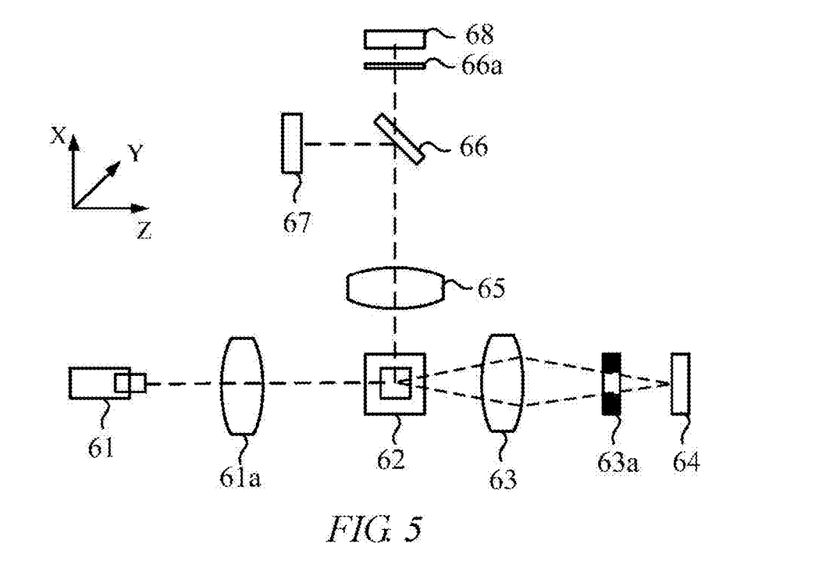
FIG. 5 is a structural schematic diagram of an optical detection portion according to an embodiment.

The flow cell 62 is configured to allow the cells in the test sample to be tested to pass through one by one. For example, in the reaction portion 30, red blood cells in the sample are hemolyzed by using one or more reagents such as the hemolytic agent, or are further stained by using the fluorescent agent, and then the cells in the prepared test sample to be tested successively pass through the flow cell 62 one by one by using a sheath flow technology. The Y-axis direction in the figure is the direction of movement of the cells in the test sample to be tested, and it should be noted that the Y-axis direction in the figure is a direction perpendicular to a paper plane. The light source 61 is configured to irradiate the cells passing through the flow cell 62. In some embodiments, the light source 61 is a laser, such as a helium-neon laser or a semiconductor laser. The light emitted by the light source 61 will be scattered all around when irradiating the cells in the flow cell 62. Therefore, when the cells in the prepared test sample to be tested pass through the flow cell 62 one by one by virtue of a sheath flow, the light emitted by the light source 61 irradiates the cells passing through the flow cell 62, and the light irradiated on the cells will be scattered all around. The forward-scattered light (for example, in a Z-axis direction in the figure) is collected by the lens group 63 to reach the photoelectric detector 64, such that an information processing portion 70 can obtain the forward-scattered light information of the cells from the photoelectric detector 64; meanwhile, in a direction perpendicular to the light irradiated on the cells, side light (for example, in an X-axis direction in the figure) is collected by the lens group 65, and the collected side light is then reflected and refracted by the dichroscope 66. Side-scattered light in the side light is reflected when passing through the dichroscope 66, and then reaches the corresponding photoelectric detector 67, and side fluorescence in the side light also reaches the corresponding photoelectric detector 68 after it is refracted or in other words, transmitted, such that the processor 50 can obtain side-scattered light information of the cells from the photoelectric detector 67 and obtain side fluorescence information of the cells from the photoelectric detector 68. Referring to FIG. 5, another example of the optical detection portion 60 is illustrated. To make the performance of the light from the light source 61 irradiated on the flow cell 62 better, a collimating lens 61a may be introduced between the light source 61 and the flow cell 62. The light emitted by the light source 61 is collimated by the collimating lens 61a and then irradiated on the cells passing through the flow cell 62. In some examples, in order to reduce noise in the collected fluorescence (that is, no interference from other light), an optical filter 66a may be further provided in front of the photoelectric detector 68, and the side fluorescence after splitting by the dichroscope 66 will reach the photoelectric detector 68 after passing through the optical filter 66a. In some embodiments, after the lens group 63 collects the forward-scattered light, a diaphragm 63a is further introduced to limit an angle of the forward-scattered light that finally reaches the photoelectric detector 64, for example, the forward-scattered light is limited to be low-angle (or in other words, small-angle) forward-scattered light.

The white blood cells can be classified and counted by using the laser scattering method, and the optical detection portion 60 described above is construed as an example. The scattered light generated by irradiating the cells with a laser beam is related to the size of the cells, the refractive index of cell membranes and the refractive index of internal structures of the cells. According to scattered light signals, a distribution diagram showing the size of blood cells and the internal information of the cells can be obtained, which is called a scattergram.

Figure 6:
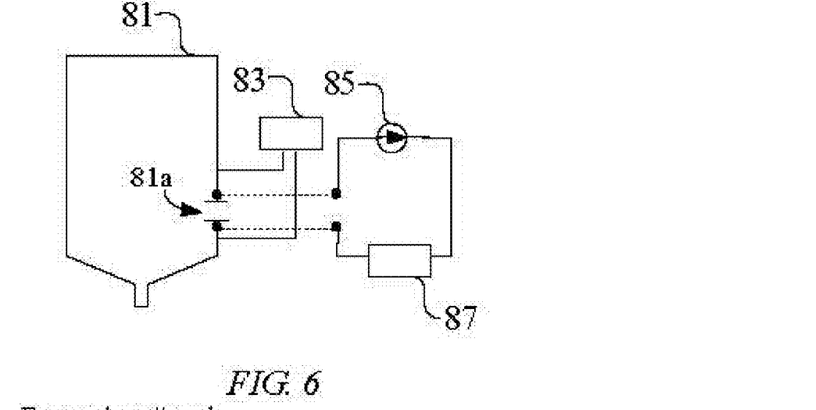
FIG. 6 is a structural schematic diagram of an impedance method-based counting component according to an embodiment.

In some embodiments, referring to FIG. 6, the impedance method-based counting component 80 includes a counting cell 81, a pressure source 83, a constant-current power source 85, and a voltage pulse detection component 87. The counting cell 81 includes a micropore 81a, and the counting cell 81 is configured to receive the test sample from the reaction portion 30. The pressure source 83 is configured to provide a pressure such that the cells contained in the test sample in the counting cell 81 pass through the micropore 81a. Two ends of the constant-current power source 85 are electrically connected to two ends of the micropore 81a, respectively. The voltage pulse detection component 87 is electrically connected to the constant-current power source 85, and is configured to detect voltage pulses generated when the cells pass through the micropore 81a.

The white blood cells can also be classified and counted by using the impedance method, and the above-described impedance method-based counting component 80 is construed as an example. By receiving voltage pulses associated with the cells, a histogram of the cells can be statistically formed so that classification and counting of the cells can be completed.

It can be seen that white blood cells can be classified and counted either by using the laser scattering method or the electrical impedance method.

The laser scattering method might as well be taken as an example. The applicant found that in the scattergram, the erythrocyte fragments are adjacent to a lymphocyte region, and only when the erythrocyte fragments are small enough, can they be distinguished from lymphocytes, and a classification result of neutrophils, lymphocytes, monocytes and eosinophils can be obtained by means of the scattergram.

For samples of animals such as a dog, a cat, a horse, a sheep, a goat, a pig and a cow, the reaction conditions for leukocyte counting and classification are the same or similar. The reaction conditions generally include an amount of a hemolytic agent, an amount of a sample, a reaction temperature and a reaction time. Under the normal or, in other words, default reaction conditions (that is, the reaction conditions commonly used and set for instruments at present), there are obvious boundaries between erythrocyte fragments and lymphocytes in most samples, and leukocyte classification results can be accurately obtained.

Taking a pig as an example, when a Duroc pig is tested, an accurate classification result can be obtained under normal reaction conditions; however, the applicant found that when a Tibetan pig is tested, the erythrocyte fragments and the lymphocyte region coincided under the default reaction conditions, and the erythrocyte fragments were involved in the lymphocyte region, resulting in high lymphocyte classification, and a leukocyte classification result cannot be accurately obtained.

Figure 7:
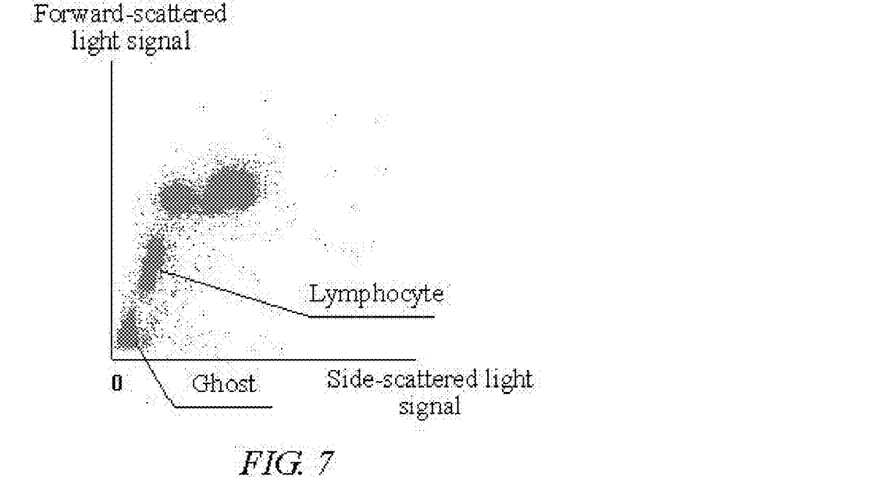
FIG. 7 is an example of a scattergram according to an embodiment.

Specifically, the locations of ghosts and lymphocytes in a mammalian sample under normal reaction conditions are shown in FIG. 7. The ghost cells and lymphocytes have clear boundaries, that is to say, the erythrocyte fragments generated under the action of the hemolytic agent is small enough not to affect the leukocyte classification and counting.

Taking a pig as an example, when a Duroc pig was subjected to reaction conditioning, it was found that with a reaction time of 30 s, the erythrocyte fragments were small enough not to affect results of leukocyte classification and counting, as shown in FIG. 7 above.

Figure 8:
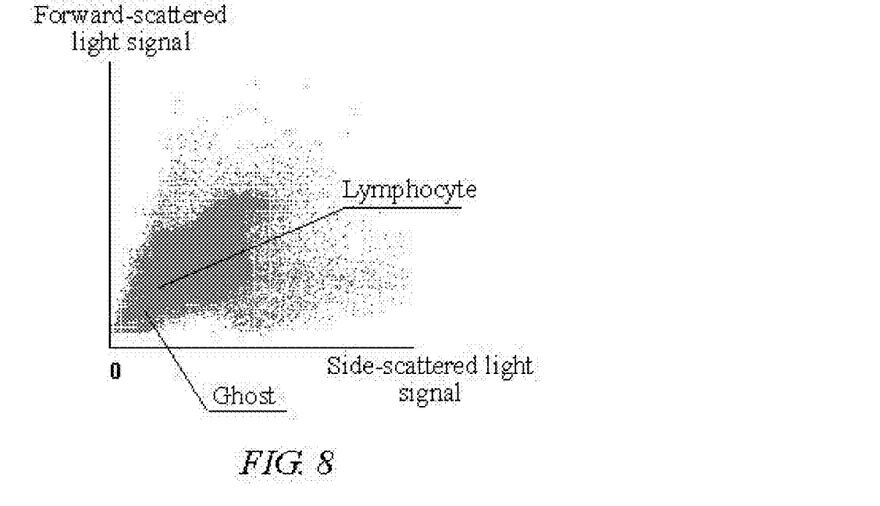
FIG. 8 is an example of a scattergram according to an embodiment.

However, when a sample of a Tibetan pig was tested under the same reaction conditions for the same reaction time of 30 s, the scattergram is shown as FIG. 8, in which erythrocyte fragments and lymphocytes are located in the same region, and it can be seen that sometimes erythrocyte fragments also enter the region where other leukocytes are located, resulting in that the leukocytes cannot be classified and counted.

It should be noted that the abscissa in FIGS. 7 and 8 represents a scattered light signal collected at a medium angle, that is, a side-scattered light signal, and the ordinate represents a scattered light signal collected at a low angle, that is, a forward-scattered light signal.

The leukocyte histogram generated from the detection data of the electrical impedance method is also similar. Under the normal reaction conditions, ghost cells and lymphocytes have clear boundaries, that is to say, the erythrocyte fragments generated under the action of the hemolytic agent are small enough not to affect the leukocyte classification and counting. However, under the normal reaction conditions, there is also a sample of which the boundaries between ghost cells and leukocytes are not obvious, resulting in inaccurate results of leukocyte classification and counting. By prolonging the reaction time, the boundaries between the erythrocyte fragments and the leukocytes can also become clear.

Thus, the sample analysis apparatus in some embodiments has multiple leukocyte measurement modes. Each of the leukocyte measurement modes includes at least the parameter of a reaction time, and different leukocyte measurement modes differ in reaction time, that is to say, the difference of different leukocyte measurement modes lies at least in different corresponding reaction times. In some embodiments, each of the leukocyte measurement modes further includes a leukocyte classification algorithm, and different leukocyte measurement modes also differ in leukocyte classification algorithm.

In some embodiments, with regard to any one current sample A to be tested, the detection and processing procedure thereof may be such that:

the processor 50 obtains the current leukocyte measurement mode for the sample A to be tested; the processor 50 sets the reaction time for the sample A to be tested according to the current leukocyte measurement mode for the sample A to be tested, that is to say, sets the reaction time for the sample A to be tested as the reaction time of the current leukocyte measurement mode therefor; the processor 50 controls the sample supply portion 10 to provide the sample A to be tested to the reaction portion 30, and controls the reagent supply portion 20 to provide a reagent containing a hemolytic agent to the reaction portion 30; the processor 50 controls the sample A to be tested and the reagent to react in the reaction portion 30 for the reaction time set for the sample to be tested A, according to the set reaction time for the sample A to be tested (that is, the reaction time of the current leukocyte measurement mode therefor), so as to prepare a test sample for detecting leukocytes; and the processor 50 controls the detection portion 40 to detect the test sample (namely, the test sample for detecting leukocytes, which is prepared from the sample A to be tested and the reagent and) so as to obtain detection data of leukocyte classification.

For example, the sample analysis apparatus has three leukocyte measurement modes, leukocyte measurement mode 1, leukocyte measurement mode 2 and leukocyte measurement mode 3, wherein the reaction time of leukocyte measurement mode 1 is 30 s, the reaction time of leukocyte measurement mode 2 is 60 s, and the reaction time of leukocyte measurement mode 3 is 90 s. If the current leukocyte measurement mode for the sample A to be tested is leukocyte measurement mode 1, the processor 50 will control the sample A to be tested and the reagent to react in the reaction portion 30 for 30 s, so as to prepare a test sample for detecting leukocytes.

Figure 9:
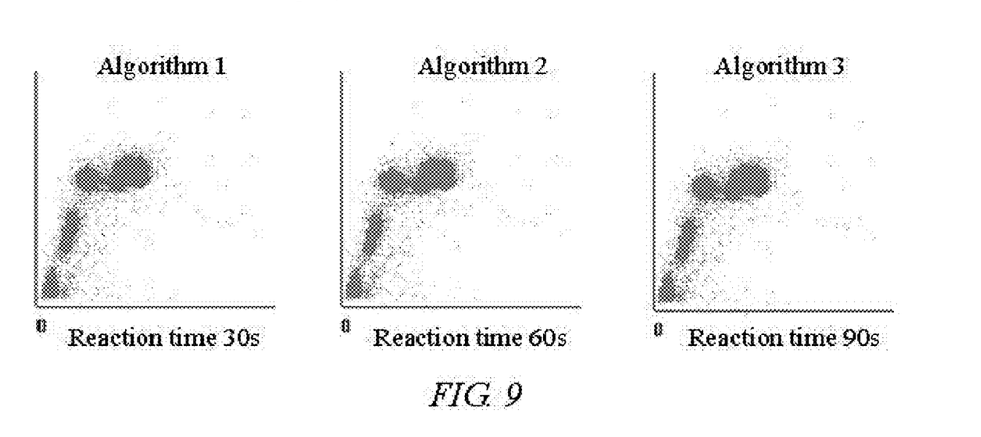
FIG. 9 is an example of scattergrams in three different leukocyte measurement modes according to an embodiment.

The processor 50 may further calculate a detection result on the basis of the detection data after obtaining the detection data of the leukocyte classification, so as to obtain a detection result of leukocyte classification. In some embodiments, the processor 50 may further process the detection data of leukocyte classification of the sample A to be tested according to the leukocyte classification algorithm of the current leukocyte measurement mode for the sample A to be tested, so as to obtain the detection result of leukocyte classification. In some embodiments, the difference of the leukocyte classification algorithms of different leukocyte measurement modes lies in that classification regions preset for different types of leukocytes are different on the scattergram. For example, FIG. 9 shows scattergrams of a same sample generated under different leukocyte measurement modes, where the reaction times of the leukocyte measurement modes from left to right are 30 s, 60 s and 90 s, respectively; with regard to a same type of leukocytes, its center of gravity is different in each figure. In general, the longer the reaction time is, the center of gravity of the same type of leukocytes tends to face the lower left; and the abscissa in FIG. 9 represents a scattered light signal collected at a medium angle, that is, a side-scattered light signal, and the ordinate represents a scattered light signal collected at a low angle, that is, a forward-scattered light signal.

Figure 10:
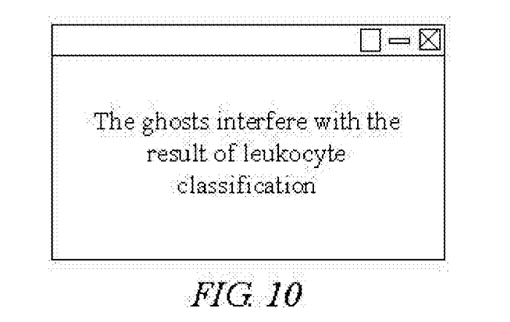
FIG. 10 is an example of sending out a prompt of ghost interference according to an embodiment.

In some embodiments, the processor 50 further determines whether the ghosts interfere with the detection result of leukocyte classification according to the detection data of leukocyte classification. If yes, the processor 50 controls to send out a prompt that the ghosts interfere with the result of leukocyte classification, and/or controls to send out a prompt for a user to switch the leukocyte measurement mode; and otherwise, if not, the processor 50 calculates and outputs the detection result of leukocyte classification. As an example in FIG. 10, when the processor 50 determines that ghosts interfere with the detection result of leukocyte classification, a corresponding prompt is sent out.

The sample A to be tested may still be taken as an example, and when it is determined that the ghosts interfere with the detection result of leukocyte classification according to the detection data of leukocyte classification of the sample A to be tested, re-detection and retest shall be performed on the sample A to be tested. The re-detection and retest of the sample A to be tested can be completed by means of automatic retest or manual retest, which will be specifically described below.

In some embodiments, when the processor 50 determines that the ghosts interfere with the detection result of leukocyte classification, the processor 50 further controls to retest the sample A to be tested in a mode different from the current leukocyte measurement mode for the sample A to be tested; and in some embodiments, the reaction time of the leukocyte measurement mode during the retest of the sample A to be tested is greater than that of the leukocyte measurement mode before the sample A to be tested is retested. For example, when the current leukocyte measurement mode for the sample A to be tested is leukocyte measurement mode 1, during measurement under this mode, if the processor 50 determines that the ghosts interfere with the detection result of leukocyte classification, the processor 50 controls to retest the sample A to be tested in other leukocyte measurement modes (such as leukocyte measurement mode 2 or leukocyte measurement mode 3) that are different from leukocyte measurement mode 1.

To coordinate with manual retesting, the sample analysis apparatus may provide a leukocyte measurement mode setting interface for samples. For example, in some embodiments, the processor 50 may further be capable of generating a leukocyte measurement mode setting interface for samples, which is configured to be operable by a user to set the sample to be tested to be in a corresponding leukocyte measurement mode.

The leukocyte measurement mode setting interface may be further configured to set leukocyte measurement modes for other samples to be tested in addition to setting the leukocyte measurement mode for the sample to be retested during manual retesting. Therefore, the leukocyte measurement mode setting interface may have the following use scenarios.

In a scenario, there is a same batch of samples A, B, C and D to be tested (for example, all samples belonging to a same subspecies), and the sample analysis apparatus will sequentially detect the samples A, B, C and D to be tested. When the ghosts interfering with the detection result of leukocyte classification are found during detection of the sample A to be tested, the user can set the leukocyte measurement mode during retesting of the sample A to be tested (for example, from the leukocyte measurement mode 1 before retesting to the leukocyte measurement mode 3 during retesting) and can further set the default leukocyte measurement mode 1 for the remaining samples B, C and D to be tested to the leukocyte measurement mode 3 by means of the leukocyte measurement mode setting interface.

In another scenario, there are a same batch of samples A, B, C and D to be tested (for example, all samples belonging to a same subspecies). Since the user knows that these samples A, B, C and D to be tested will have detection results of leukocyte classification interfering with the ghosts under the ordinary reaction conditions, at a sample requesting stage, leukocyte measurement modes for these samples A, B, C and D to be tested are set as, for example, leukocyte measurement mode 3.

Figure 11:
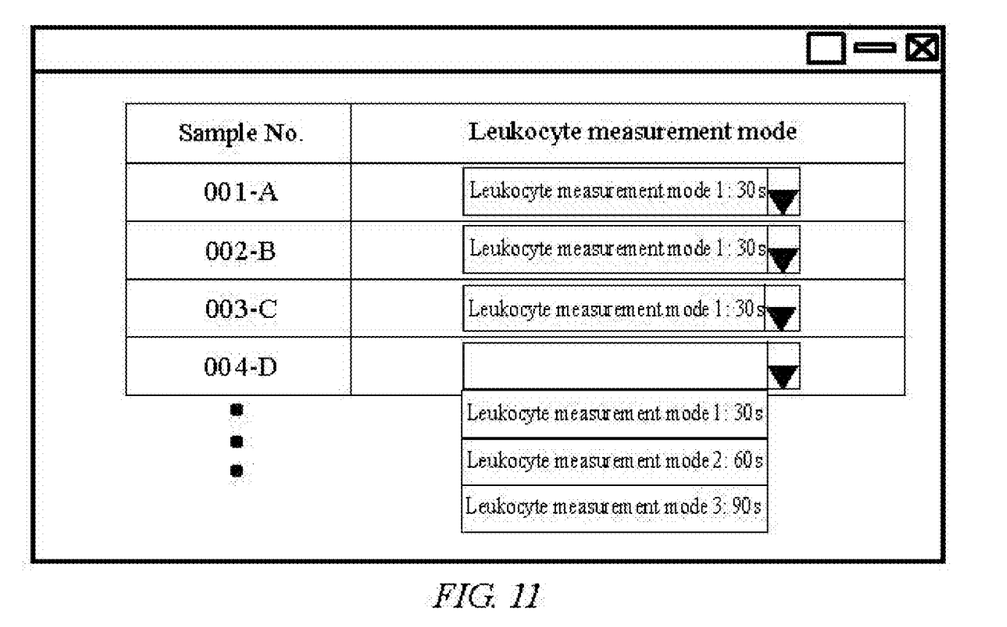
FIG. 11 is an example of a leukocyte measurement mode setting interface for samples according to an embodiment.

FIG. 11 is an example of the leukocyte measurement mode setting interface, and the user can set the leukocyte measurement mode for each sample to be tested by means of a dropdown box.

The sample analysis apparatus in some embodiments of the disclosure is configured to analyze samples of one or more animals, and with regard to at least one of the animals, the sample analysis apparatus has a plurality of leukocyte measurement modes, each of which includes at least a reaction time, and different leukocyte measurement modes for a same animal have different reaction times. In some embodiments, each of the leukocyte measurement modes further includes a leukocyte classification algorithm, and different leukocyte measurement modes have different leukocyte classification algorithms.

In some embodiments, with regard to any one current sample A to be tested, the detection and processing procedure thereof may be such that:

the processor 50 obtains a current leukocyte measurement mode for the sample A to be tested; the processor 50 sets the reaction time for the sample A to be tested according to the current leukocyte measurement mode for the sample A to be tested, that is to say, sets the reaction time for the sample A to be tested as the reaction time for the current leukocyte measurement mode therefor; the processor 50 controls the sample supply portion 10 to provide the sample A to be tested to the reaction portion 30, and controls the reagent supply portion 20 to provide a reagent containing a hemolytic agent to the reaction portion 30; the processor 50 controls the sample A to be tested and the reagent to react in the reaction portion 30 for the reaction time set for the sample to be tested A, according to the set reaction time for the sample to be tested A (that is, the reaction time of the current leukocyte measurement mode therefor), so as to prepare a test sample for detecting leukocytes; and the processor 50 controls the detection portion 40 to detect the test sample (namely, the test sample for detecting leukocytes, which is prepared from the sample A to be tested and the reagent), so as to obtain detection data of leukocyte classification.

For example, the sample A to be tested is a pig sample. For pigs, the sample analysis apparatus has three leukocyte measurement modes, leukocyte measurement mode 1, leukocyte measurement mode 2 and leukocyte measurement mode 3, wherein the reaction time of leukocyte measurement mode 1 is 30 s, the reaction time of leukocyte measurement mode 2 is 60 s, and the reaction time of leukocyte measurement mode 3 is 90 s. If the current leukocyte measurement mode for the sample A to be tested is leukocyte measurement mode 1, the processor 50 controls the sample A to be tested and the reagent to react in the reaction portion 30 for 30 s, so as to prepare a test sample for detecting leukocytes.

The processor 50 may further calculate a detection result on the basis of the detection data after obtaining the detection data of the leukocyte classification, so as to obtain a detection result of leukocyte classification. In some embodiments, the processor 50 may further process the detection data of leukocyte classification of the sample A to be tested according to the leukocyte classification algorithm of the current leukocyte measurement mode for the sample A to be tested so as to obtain the detection result of leukocyte classification. In some embodiments, the difference of the leukocyte classification algorithms of different leukocyte measurement modes lies in that classification regions preset for different types of leukocytes are different on the scattergram.

In some embodiments, the processor 50 further determines whether the ghosts interfere with the detection result of leukocyte classification according to the detection data of leukocyte classification. If yes, the processor 50 controls to send out a prompt that the ghosts interfere with the result of leukocyte classification, and/or controls to send out a prompt for a user to switch the leukocyte measurement mode; and otherwise, if not, the processor 50 calculates and outputs the detection result of leukocyte classification. For example, FIG. 10 above shows an example, when the processor 50 determines that ghosts interfere with the detection result of leukocyte classification, a corresponding prompt is sent out.

The sample A to be tested may still be taken as an example, and when it is determined that the ghosts interfere with the detection result of leukocyte classification according to the detection data of leukocyte classification of the sample A to be tested, re-detection and retest shall be performed on the sample A to be tested. The re-detection and retest of the sample A to be tested can be completed by means of automatic retest or manual retest, which will be specifically described below.

In some embodiments, when the processor 50 determines that the ghosts interfere with the detection result of leukocyte classification, the processor 50 further controls to retest the sample A to be tested in a mode different from the current leukocyte measurement mode for the sample A to be tested; and in some embodiments, the reaction time of the leukocyte measurement mode during the retest of the sample A to be tested is greater than that of the leukocyte measurement mode before the sample A to be tested is retested. For example, when the current leukocyte measurement mode for the sample A to be tested is leukocyte measurement mode 1, during measurement under this mode, if the processor 50 determines that the ghosts interfere with the detection result of leukocyte classification, the processor 50 controls to retest the sample A to be tested in other leukocyte measurement modes (such as leukocyte measurement mode 2 or leukocyte measurement mode 3) that are different from leukocyte measurement mode 1.

To coordinate with manual retesting, the sample analysis apparatus may provide a leukocyte measurement mode setting interface during retesting, allowing a user to operate so as to set the leukocyte measurement mode for the sample to be retested.

Figure 12:
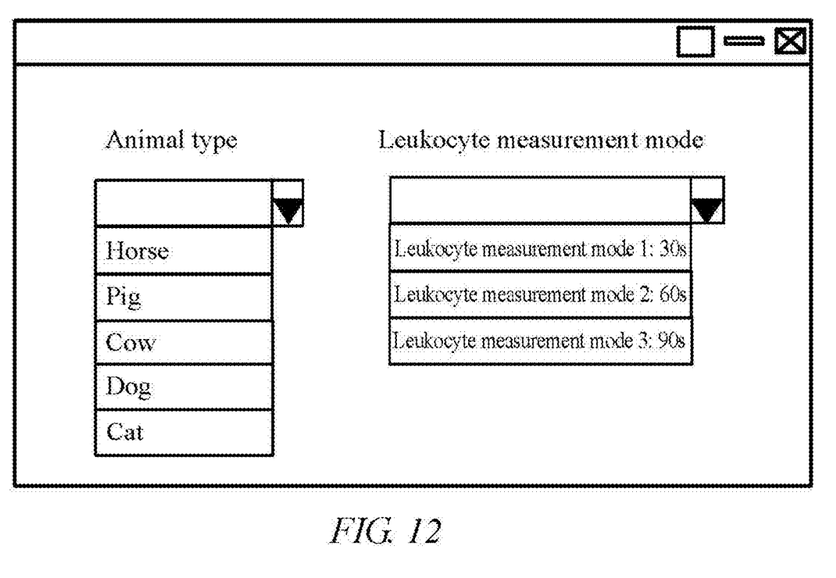
FIG. 12 is an example of a leukocyte measurement mode setting interface according to an embodiment.
Figure 13:
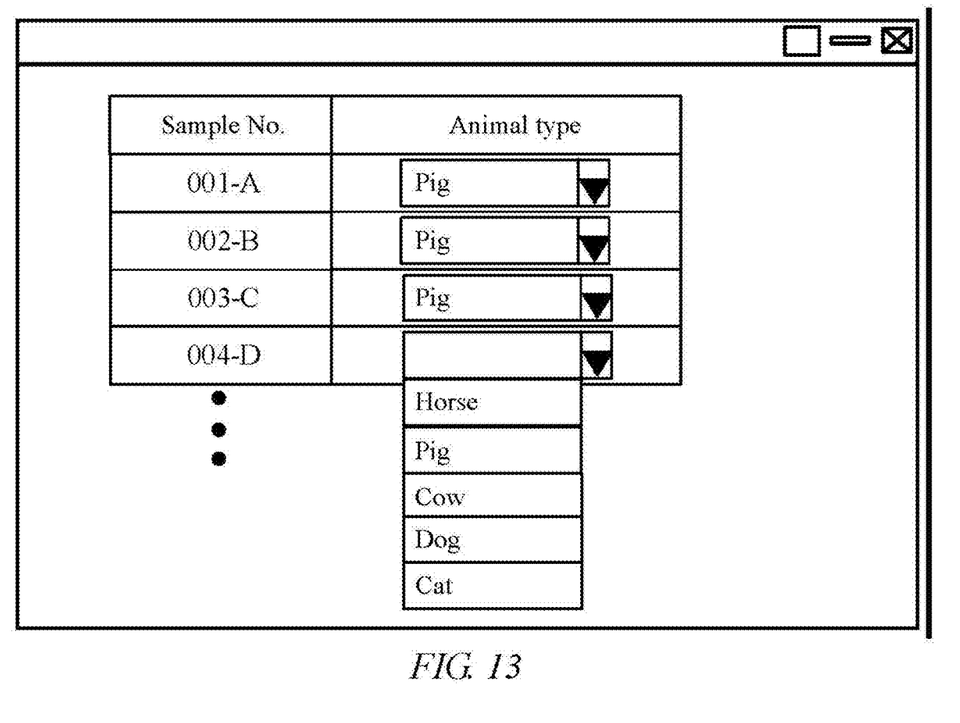
FIG. 13 is an example of a sample requesting interface according to an embodiment.

In other embodiments, the sample analysis apparatus may further provide a leukocyte measurement mode setting interface. For example, in some embodiments, the processor 50 are further capable of generating the leukocyte measurement mode setting interface configured to be operable by a user to set a leukocyte measurement mode for an animal. In some embodiments, referring to FIG. 12, the leukocyte measurement mode setting interface includes an animal type entry operable by a user to set an animal type, and a reaction time entry operable by the user to set a leukocyte measurement mode corresponding to the animal type. In some embodiments, the processor 50 is further capable of generating a sample requesting interface operable by a user to set a sample to be tested to be of a corresponding animal type, as shown for example in FIG. 13. It can be seen that the sample to be tested can be set to be of the corresponding animal type by means of the sample requesting interface, and the corresponding leukocyte measurement mode can be set for the animal type by means of the leukocyte measurement mode setting interface, and accordingly the setting of the leukocyte measurement mode for the sample can be finally completed.

It can be seen that, with regard to some or all animal species, the sample analysis apparatus in some embodiments can set the reaction time for each animal species, and set several different reaction times; and the user can set the reaction time for an animal according to the characteristics of the sample, which can not only take into account the test speed, but also ensure the accuracy of classification results.

Figure 14:
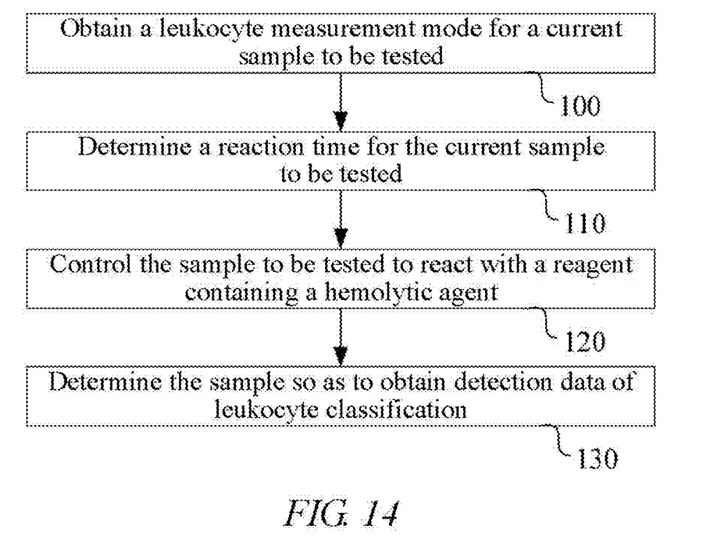
FIG. 14 is a flowchart of a sample analysis method according to an embodiment.

A sample analysis method is further disclosed in some embodiments of the disclosure. Referring to FIG. 14, the sample analysis method in some embodiments includes the following steps:

Step 100, obtaining a leukocyte measurement mode for a current sample to be tested (hereinafter may be referred to as the sample A to be tested); where the sample analysis method has a plurality of leukocyte measurement modes, each of the leukocyte measurement modes includes at least a reaction time, and different leukocyte measurement modes have different reaction times.

Step 110, determining, according to the leukocyte measurement mode for the current sample A to be tested, a reaction time for the current sample A to be tested.

Step 120, controlling, according to the determined reaction time for the sample A to be tested, the sample A to be tested to react with a reagent containing a hemolytic agent, so as to prepare a test sample for detecting leukocytes; that is, the sample A to be tested reacts with the reagent containing the hemolytic agent for the reaction time of the leukocyte measurement mode for the sample A to be tested, and accordingly the test sample for detecting leukocytes is prepared.

Step 130, controlling to detect the test sample for detecting leukocytes, so as to obtain detection data of leukocyte classification.

Figure 15:
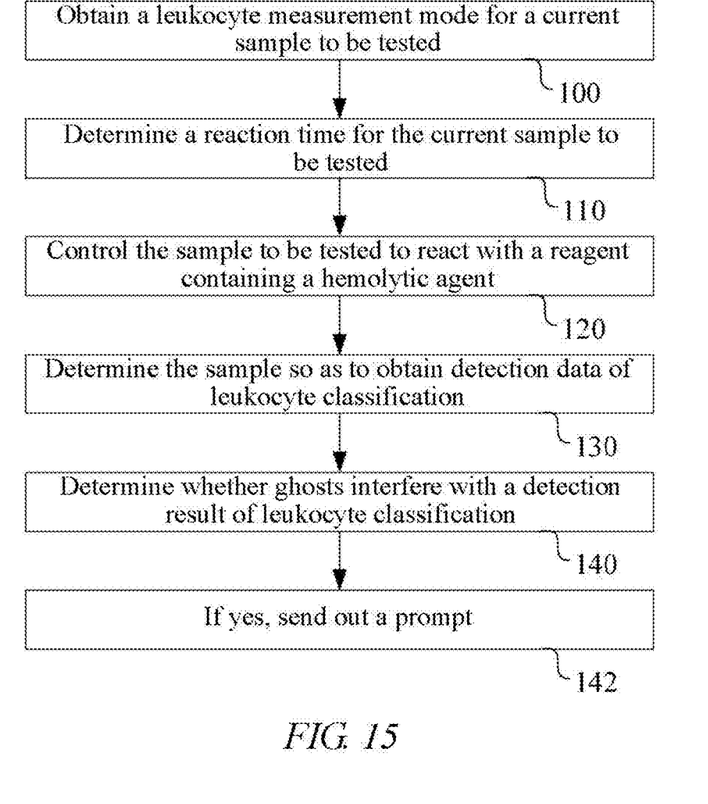
FIG. 15 is a flowchart of a sample analysis method according to an embodiment.

Referring to FIG. 15, the sample analysis method in some embodiments further includes the following steps:

Step 140, determining whether the ghosts interfere with a detection result of leukocyte classification according to the detection data of leukocyte classification.

If yes, step 142 is executed: controlling to send out a prompt. For example, in step 142, it is controlled to send out a prompt that the ghosts interfere with the result of leukocyte classification, and/or it is controlled to send out a prompt for a user to switch the leukocyte measurement mode.

Figure 16:
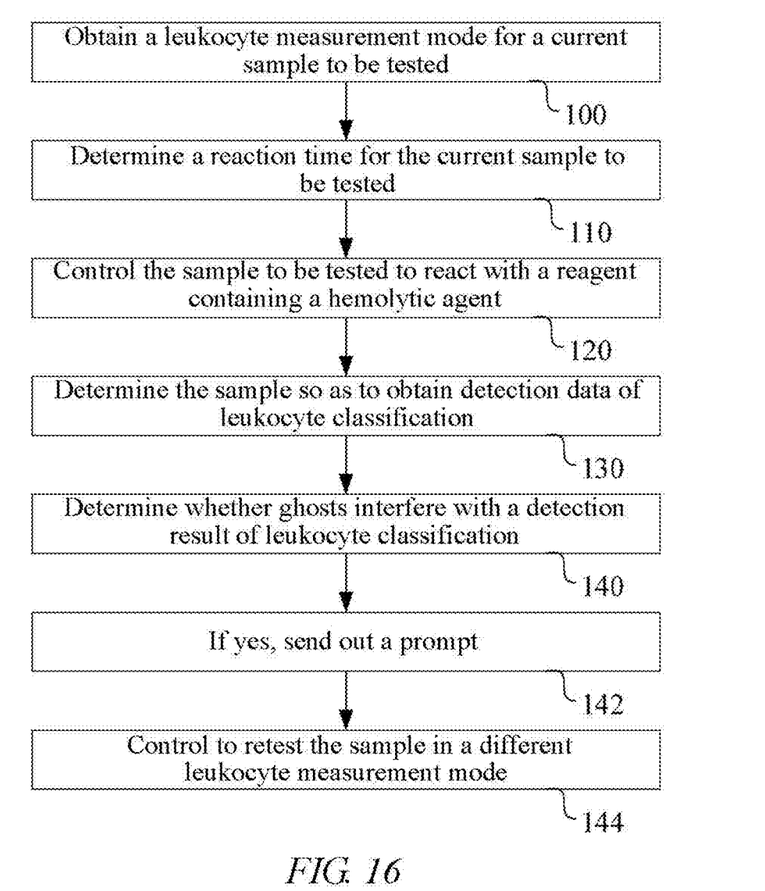
FIG. 16 is a flowchart of a sample analysis method according to an embodiment.

Referring to FIG. 16, the sample analysis method in some embodiments further includes the following steps:

Step 144, controlling to retesting, when determining that the ghosts interfere with the detection result of leukocyte classification, the sample A to be tested in a mode different from the current leukocyte measurement mode for the sample A to be tested. In some embodiments, the reaction time of the leukocyte measurement mode during the retest of the sample A to be tested is greater than that of the leukocyte measurement mode before the sample A to be tested is retested. For example, when the current leukocyte measurement mode for the sample A to be tested is leukocyte measurement mode 1, during measurement in this mode, if it is determined in step 140 that the ghosts interfere with the detection result of leukocyte classification, step 144 is executed to control to retest the sample A to be tested in other leukocyte measurement modes (such as leukocyte measurement mode 2 or leukocyte measurement mode 3) that are different from leukocyte measurement mode 1.

Figure 17:
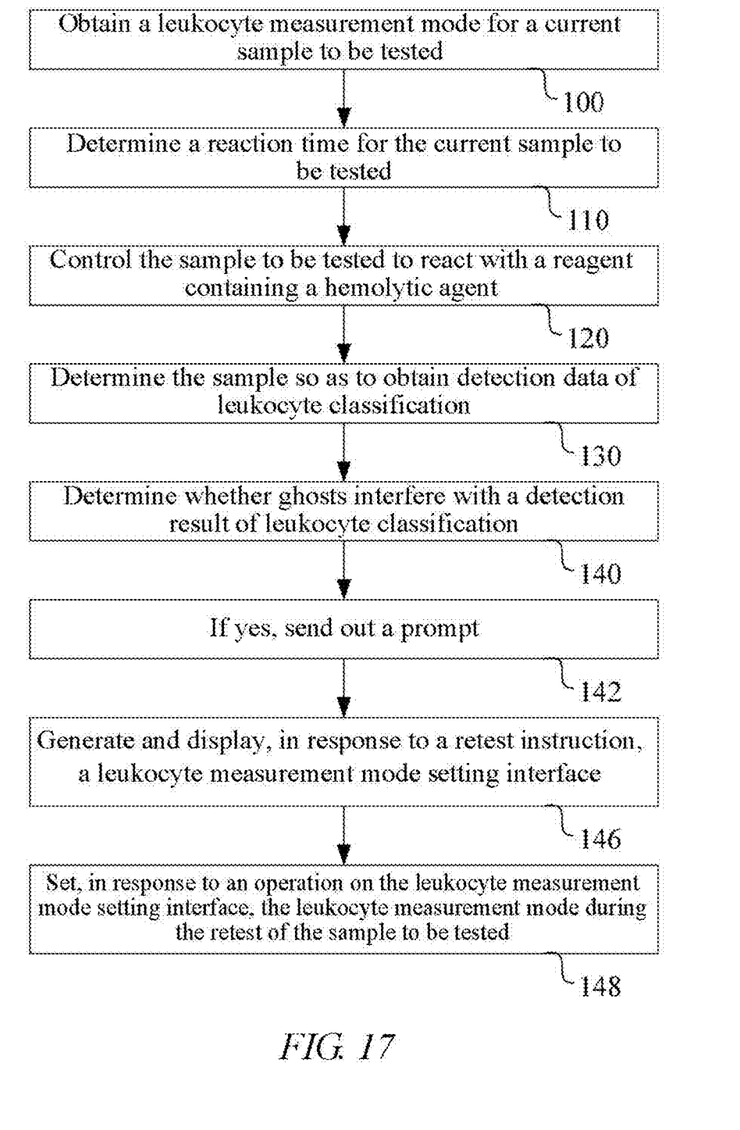
FIG. 17 is a flowchart of a sample analysis method according to an embodiment.

Referring to FIG. 17, the sample analysis method in some embodiments further includes the following steps:

Step 146, generating and displaying, in response to a retest instruction, a leukocyte measurement mode setting interface; the leukocyte measurement mode setting interface displaying the reaction time before the sample to be tested is retested; and Step 148, setting, in response to an operation on the leukocyte measurement mode setting interface, the leukocyte measurement mode during the retest of the sample to be tested.

In some embodiments, each of the leukocyte measurement modes further includes a leukocyte classification algorithm, and different leukocyte measurement modes have different leukocyte classification algorithms. The sample analysis method further includes a step of processing the detection data of leukocyte classification according to the leukocyte classification algorithm of the current leukocyte measurement mode for the sample to be tested, so as to obtain a detection result of leukocyte classification. In some embodiments, the difference of the leukocyte classification algorithms of different leukocyte measurement modes lies in that classification regions preset for different types of leukocytes are different on the scattergram.

Descriptions are provided herein with reference to various exemplary embodiments. However, those skilled in the art should understand that changes and corrections may be made to the exemplary embodiments without departing from the scope of this specification. For example, various operational steps and assemblies for executing the operational steps may be implemented in different manners on the basis of specific applications or in consideration of any number of functions associated with operations of the system (for example, one or more steps may be deleted, modified or incorporated into other steps).

In the foregoing embodiments, the disclosure may be implemented in whole or in part by software, hardware, firmware, or any combination thereof. In addition, as those skilled in the art can understand, the principles herein may be reflected in a computer program product in a computer-readable storage medium, where the readable storage medium is loaded with computer-readable program codes in advance. Any tangible, non-transitory computer-readable storage medium can be used, including magnetic storage devices (hard disks, floppy disks, etc.), optical storage devices (CD-ROM, DVD, Blu Ray disks, etc.), flash memories, and/or the like. These computer program instructions may be loaded on a general-purpose computer, a special-purpose computer, or other programmable data processing devices to form a machine, such that these instructions being executed on a computer or other programmable data processing apparatuses may produce an apparatus for implementing specified functions. These computer program instructions may alternatively be stored in a computer-readable memory. The computer-readable memory may instruct a computer or other programmable data processing devices to operate in a particular manner, such that the instructions stored in the computer-readable memory may produce an article of manufacture which includes an implementing apparatus for implementing specified functions. The computer program instructions may alternatively be loaded onto a computer or other programmable data processing devices and thereby to perform a series of operational steps on the computer or other programmable devices to produce a computer-implemented process, such that the instructions being executed on the computer or other programmable devices may provide steps for implementing specified functions.

Although the principles herein are shown in various embodiments, many modifications of structures, arrangements, proportions, elements, materials, and components particularly applicable to specific environmental and operational requirements may be used without departing from the principles and scope of the disclosure. The above modifications and other changes or corrections fall within the scope of this specification.

The foregoing detailed descriptions are provided with reference to various embodiments. However, those skilled in the art should understand that various corrections and changes may be made without departing from the scope of the disclosure. Therefore, the consideration of the disclosure should be made on an illustrative meaning other than a limited meaning, and all these modifications should fall within the scope of the disclosure. Similarly, the advantages, other advantages, and solutions to problems of the various embodiments are described above. However, the benefits, the advantages, the solutions to the problems, and any of their contributing factors, or solutions clarifying them should not be construed to be critical, necessary, or essential. The term "include" used herein and any other variations thereof all refer to a non-exclusive inclusion, such that a process, method, article, or device including a list of elements includes not only these elements, but also other elements that are not expressly listed or not inherent to the process, method, system, article, or device. In addition, the term "couple" used herein and any other variations thereof refer to a physical connection, an electrical connection, a magnetic connection, an optical connection, a communication connection, a functional connection, and/or any other connections.

Those skilled in the art should understand that many changes may be made to the details of the foregoing embodiments without departing from the basic principles of the disclosure. Therefore, the scope of the disclosure may be determined by the claims.

The invention claimed is:

1. A sample analysis apparatus, the sample analysis apparatus being configured to analyze samples of one or more animals; the sample analysis apparatus comprising:
   a sample supply portion configured to supply a sample to be tested including
      (a) a blood sample or
      (b) a body fluid sample to be tested;
   a reagent supply portion configured to supply a reagent;
   a reaction portion configured to provide a reaction place for the sample to be tested and the reagent so as to prepare a test sample formed by reaction of the sample to be tested and the reagent;
   a detection portion configured to detect the test sample so as to obtain detection data; and
   a processor configured to calculate a detection result according to the detection data from
      (a) a plurality of leukocyte measurement modes for the blood sample of at least one of the one or more animals, wherein each of the leukocyte measurement modes for the blood sample comprises a reaction time and different leukocyte measurement modes for the blood sample of a single animal having different reaction times, or
      (b) a plurality of leukocyte measurement modes for the body fluid sample of at least one of the one or more animals, wherein each of the leukocyte measurement modes for the body fluid sample comprises a reaction time and different leukocyte measurement modes for the body fluid sample of a single animal having different reaction times; wherein the processor obtains a current leukocyte measurement mode for the sample of the single animal to be tested;
   the processor controls the sample supply portion to provide the sample to be tested to the reaction portion, and controls the reagent supply portion to provide the reagent containing a hemolytic agent to the reaction portion;
   the processor controls the sample to be tested and the reagent to react in the reaction portion according to the reaction time set in the current leukocyte measurement mode for the sample to be tested, so as to prepare the test sample for detecting leukocytes;
   the processor controls the detection portion to detect the test sample so as to obtain detection data of leukocyte classification and the processor processes the detection data to obtain a detection result of the leukocyte classification; and
   the processor determines whether erythrocyte fragments in the test sample interfere with the detection result of leukocyte classification according to the detection data of leukocyte classification; and
   upon determining the erythrocyte fragments are interfering, the processor controls to send out a prompt to an interface for a user that the erythrocyte fragments interfere with the detection result of leukocyte classification, and/or controls to send out a prompt to an interface for a user to switch the leukocyte measurement mode.

2. The sample analysis apparatus of claim 1, wherein each of the leukocyte measurement modes further comprises a leukocyte classification algorithm, and different leukocyte measurement modes for a same animal have different leukocyte classification algorithms; and
   the processor processes the detection data of leukocyte classification according to the leukocyte classification algorithm of the current leukocyte measurement mode for the sample to be tested, so as to obtain the detection result of leukocyte classification.

3. The sample analysis apparatus of claim 1, wherein when determining that the erythrocyte fragments interfere with the detection result of leukocyte classification, the processor further controls to retest the sample to be tested in a mode different from the current leukocyte measurement mode for the test sample.

4. The sample analysis apparatus of claim 3, wherein the reaction time of the leukocyte measurement mode during the retest of the sample to be tested is greater than that of the leukocyte measurement mode before the sample to be tested is retested.

5. The sample analysis apparatus of claim 1, wherein the sample analysis apparatus further comprises a leukocyte measurement mode setting interface in communication with the processor configured to be operable by the user to set a leukocyte measurement mode for an animal.

6. The sample analysis apparatus of claim 5, wherein the leukocyte measurement mode setting interface comprises an animal type entry operable by the user to set an animal type, and a reaction time entry operable by the user to set a leukocyte measurement mode corresponding to the animal type.

7. The sample analysis apparatus of claim 5, wherein the sample analysis apparatus further comprises a sample requesting interface in communication with the processor configured to be operable by the user to set the sample to be tested to be of a corresponding animal type.

* * * * *